US00PP10736P

United States Patent [19]

McCullough

[11] Patent Number: Plant 10,736

[45] Date of Patent: Dec. 22, 1998

[54] BEGONIA PLANT NAMED 'LADY ROSE'

[75] Inventor: Terry McCullough, Brenham, Tex.

[73] Assignee: Turkey Creek Farms, Inc., Humble, Tex.

[21] Appl. No.: 870,004

[22] Filed: Jun. 6, 1997

[51] Int. Cl.[6] ..... A01H 5/00

[52] U.S. Cl. ..... Plt./87.17

[58] Field of Search ..... Plt./87.17

*Primary Examiner*—Howard J. Locker

*Assistant Examiner*—Melissa L. Kimball

*Attorney, Agent, or Firm*—C. A. Whealy

[57] ABSTRACT

A distinctive cultivar of Begonia plant named Lady Rose, characterized by its numerous fully double hot pink flowers; upright, spreading and freely branching growth habit; dark green foliage; and strong and vigorous root system.

2 Drawing Sheets

The present invention relates to a new and distinctive cultivar of Begonia plant, botanically known as *Begonia semperflorens*, and hereinafter referred to by the cultivar name Lady Rose.

The new cultivar was discovered by the inventor in Humble, Tex., as a naturally-occurring mutation of the nonpatented *Begonia semperflorens* cultivar Lady Carol, and was observed in a group of flowering plants of the parent cultivar in March, 1996.

Asexual reproduction of the new cultivar by cuttings in Humble, Tex., has shown that the unique features of this new Begonia are stable and are reproduced true to type in successive propagations.

The new cultivar has not been observed under all possible environmental conditions. The phenotype may vary significantly with variations in environment such as temperature and light level, without, however, any variance in genotype.

The following traits have been repeatedly observed and are determined to be the unique characteristics of 'Lady Rose':

1. Numerous fully double hot pink flowers.
2. Upright and spreading growth habit.
3. Freely branching.
4. Dark green foliage.
5. Strong and vigorous root system.

The following characteristics differentiate the new cultivar from the parent cultivar Lady Carol and other Begonias commercially known and used in the floriculture industry, namely the nonpatented cultivar Lady Frances:

1. Plants of the new cultivar are less vigorous and shorter than plants of the cultivar Lady Carol.

2. Flower color of the new cultivar is hot pink whereas flower color of the plants of the cultivars Lady Carol and Lady Frances is brigh red and light pink, respectively.

3. Foliage of plants of the new cultivar is greener, not as bronze, and less glossy than foliage of plants of the cultivars Lady Carol and Lady Frances.

The accompanying colored photographs illustrate the overall appearance and flower color of the new cultivar, showing the colors as true as it is reasonably possible to obtain in colored reproductions of this type.

The first photograph comprises a side perspective view of a typical potted plant of 'Lady Rose'.

The second photograph comprises a side perspective view of typical flowering pots of the cultivars Lady Frances, Lady Rose and Lady Carol (left to right).

The third photograph comprises a close-up view of typical flowers of the cultivars Lady Frances, Lady Rose and Lady Carol (left to right).

The fourth photograph comprises a close-up view of typical leaves of the cultivars Lady Frances, Lady Rose and Lady Carol (left to right). Actual flower and foliage colors may differ from flower and foliage colors in the photographs due to light reflectance.

The following observations, measurements, values, and comparisons describe plants grown in Humble, Tex., during the spring under commercial practice in a polyethylene-covered greenhouse. Day and night temperatures ranged from 18° to 21° C. and 14° to 17° C., respectively, and light levels were maintained at 3,500 to 4,000 footcandles. In the following description, color references are made to The Royal Horticultural Society Colour Chart except where general terms of ordinary dictionary significance are used.

Botanical classification: *Begonia semperflorens* cultivar Lady Rose.

Parentage: Naturally-occurring mutation of nonpatented *Begonia semperflorens* cultivar Lady Carol.

Propagation:

*Type.*—By cuttings.

*Time to initiate roots.*—10 and 15 days at temperatures of 27° and 18° C., respectively.

*Time to develop roots.*—15 to 25 days at temperatures of 24° and 16° C., respectively.

Plant description:

*Plant form.*—Upright and spreading potted plant, freely branching. Good stem and stem base strength. Flowers are fully double and abundant. Plants flower continuously under warm night temperatures.

*Growth habit.*—Moderate. Suitable for 10-cm and larger containers.

*Plant height.*—About 20 cm in a 12.5-cm pot.

*Rooting habit.*—Root system is very strong, vigorous, and develops rapidly. Roots are thick and fleshy.

*Plant width.*—About 26 cm in a 12.5-cm pot.

*Stem description.*—Lateral branch length: About 14 cm. Lateral branch diameter: About 8 mm. Internode length: About 1.5 cm. Stem color: 144A/146A. Stem texture: Glabrous. Stem strength: Moderate.

*Foliage description.*—Leaf arrangement: Simple, alternate. Leaf length: About 9 cm. Leaf width: About 9.5 cm. Leaf shape: Asymmetrical, roughly ovate. Leaf apex: Acute to rounded. Leaf base: Obtuse. Leaf margin: Finely serrate/pectinate. Leaf texture: Glabrous, iridescent. Leaf color: Young foliage, adaxial surface: Reddish brown/green, close to 187A with 146A. Young foliage, abaxial surface: 187A. Mature foliage, adaxial surface: Darker than 147A with reddish brown tones. Mature foliage, abaxial surface: 187A with green tones. Venation, adaxial surface: 146A. Venation, abaxial surface: 146A. Petiole length: About 3.3 cm. Petiole diameter: About 5 mm. Petiole color: 146B/144A.

Flower description:

*Flowering habit.*—Flowers arranged in racemes. Many racemes in flower simultaneously. Flowering continuous under warm night temperatures. Flowers of self-cleaning.

*Natural flowering season.*—Plants will flower year around regardless of daylength, however plants will flower earlier and more abundantly if night temperatures are warm.

*Quantity of flowers.*—Numerous, potentially 20 to 25 per branch.

*Flowers.*—Shape: Rounded to oblong. Diameter: About 3 cm. Height: About 1.5 cm. Aspect: Upright to outwardly facing.

*Peduncle.*—Length: About 1.5 cm. Diameter: About 1 mm. Strength: Weight of flowers may cause peduncles to droop. Texture: Smooth, waxy. Color: 63A to light pink.

*Flower bud.*—Shape: Rounded cordate. Diameter: About 1.3 cm. Length: About 9 mm. Color: 63A, iridescent.

*Petals.*—Arrangement: Rosette. Shape: Flat, ovate. Quantity per flower: Numerous. Length: About 1.5 cm. Width: About 1 cm. Apex: Rounded. Margin: Entire to slightly crenate. Texture: Smooth, satiny, iridescent. Color: When opening: Abaxial and adaxial surfaces: 63A. Fully open: Abaxial surface: 63A at apex, white at base. Adaxial surface: 63A at apex, white at base.

*Tepals.*—Arrangement: Opposite. Shape: Rounded, flat. Quantity per flower: Two. Length: About 1.5 cm. Width: About 1.8 cm. Apex: Rounded. Margin: Entire. Texture: Smooth, satiny, iridescent. Color: 63A at apex, white at base.

*Sepals.*—Arrangement: Opposite. Shape: Linear. Quantity per flower: Two. Apex: Rounded. Margin: Ciliate. Texture: Thin, translucent. Color: Light green, close to 144A.

*Reproductive organs.*—None.

Disease resistance: Resistance to known pathogens of Begonia has not been observed.

Seed production: Seed production has not been observed as reproductive organs are not formed.

I claim:

1. A new and distinct Begonia plant named Lady Rose, as illustrated and described.

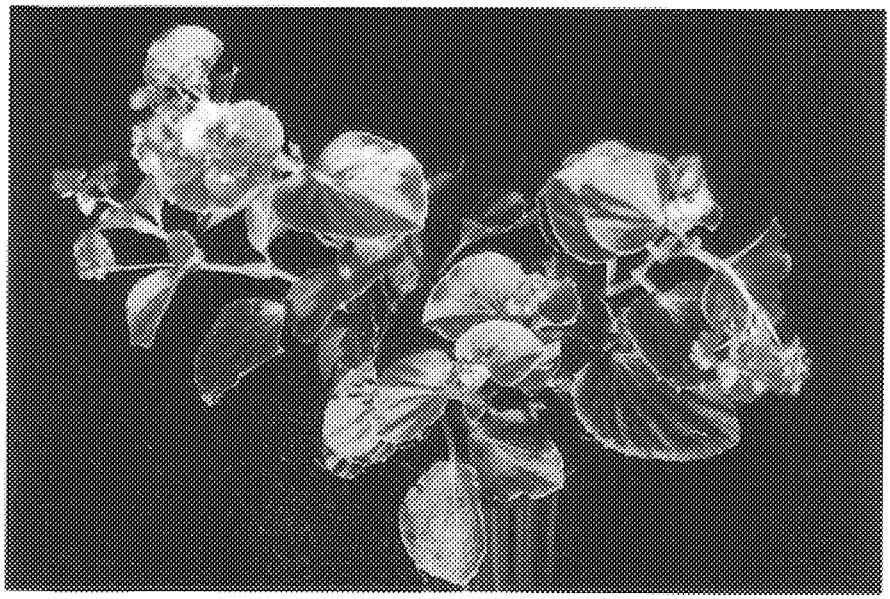
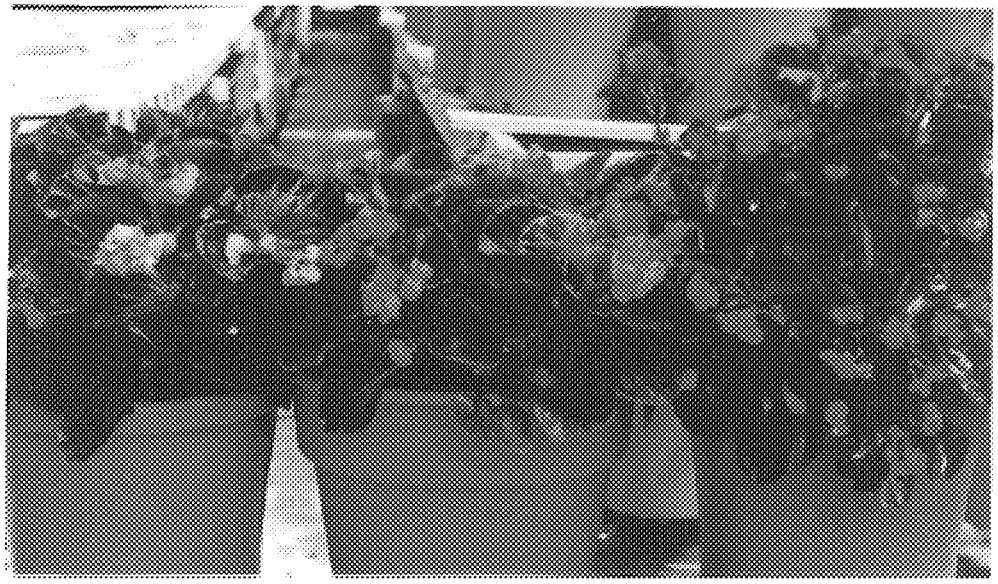

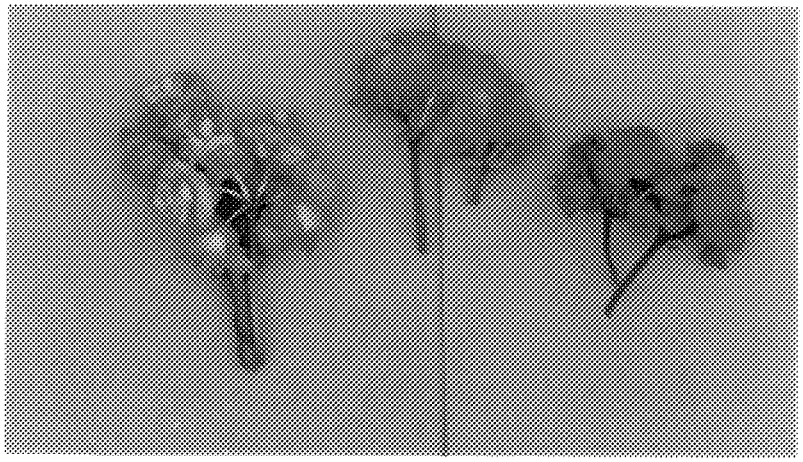
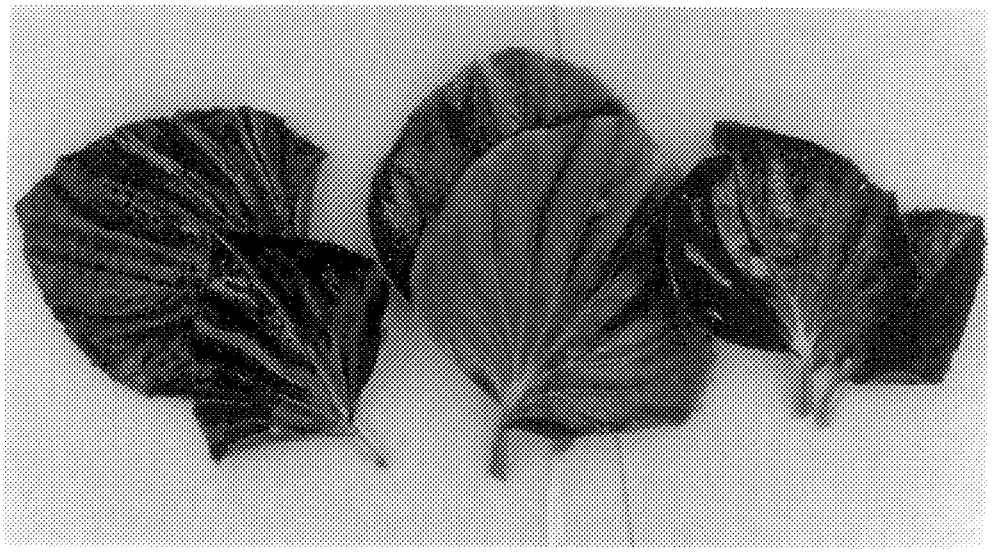

* * * * *